US011802282B2

(12) United States Patent
Wang et al.

(10) Patent No.: US 11,802,282 B2
(45) Date of Patent: Oct. 31, 2023

(54) METHOD FOR IDENTIFYING GENE FUSIONS BY CIRCLE CDNA AMPLIFICATION

(71) Applicant: XBF LLC, Phoenix, MD (US)

(72) Inventors: Xiao Bing Wang, Sparks Glencoe, MD (US); Xiao Fei Li, Sparks Glencoe, MD (US)

(73) Assignee: XBF LLC, Phoenix, MD (US)

( * ) Notice: Subject to any disclaimer, the term of this patent is extended or adjusted under 35 U.S.C. 154(b) by 0 days.

(21) Appl. No.: 17/099,093

(22) Filed: Nov. 16, 2020

(65) Prior Publication Data

US 2021/0147834 A1 May 20, 2021

Related U.S. Application Data

(60) Provisional application No. 62/974,193, filed on Nov. 19, 2019.

(51) Int. Cl.
*C12N 15/10* (2006.01)
*C12Q 1/6853* (2018.01)

(52) U.S. Cl.
CPC ....... *C12N 15/1096* (2013.01); *C12Q 1/6853* (2013.01); *C12Q 2521/107* (2013.01); *C12Q 2521/301* (2013.01); *C12Q 2521/501* (2013.01); *C12Q 2531/113* (2013.01); *C12Q 2531/125* (2013.01)

(58) Field of Classification Search
CPC ............ C12Q 1/6853; C12Q 2521/107; C12Q 2521/301; C12Q 2521/501; C12Q 2531/113; C12Q 2531/125; C12Q 1/6827
See application file for complete search history.

(56) References Cited

U.S. PATENT DOCUMENTS

2004/0058330 A1* 3/2004 Aevarsson ............. C12P 19/34 435/6.12
2009/0068652 A1 3/2009 Taylor et al.
2016/0304954 A1 10/2016 Lin et al.
2017/0191123 A1* 7/2017 Kim ....................... G01N 33/53
2018/0298434 A1 10/2018 Weng et al.

FOREIGN PATENT DOCUMENTS

WO 2021/101835 A1 5/2021

OTHER PUBLICATIONS

Maruyama et al. cRACE: a simple method for identification of the 5' end of mRNAs. Nucleic Acids Research 1995; 23: 3796-3797 (Year: 1995).*
Lee et al. CUT-PCR: CRISPR-mediated, ultrasensitive detection of target DNA using PCR. Oncogene 2017; 36: 6823-6829 (Year: 2017).*
Huang et al. A simple method for direct cloning cDNA sequence that flanks a region of known sequence from total RNA by applying the inverse polymerase chain reaction. Nucleic Acids Research 1990; 18: 1922 (Year: 1990).*
International Search Report and Written Opinion in PCT/US20/60712 (16 pages).

* cited by examiner

*Primary Examiner* — Angela M. Bertagna
(74) *Attorney, Agent, or Firm* — Smith, Gambrell & Russell; Judy Jarecki-Black

(57) ABSTRACT

One embodiment provides methods to identify known and unknown gene fusions by creating a cDNA circle and analyzing the circle cDNA by amplification or sequencing. The circle cDNA is created in two approaches: 1) reverse transcribe a target RNA to cDNA, ligate the 3'end of the cDNA to its 5'end to form a circle cDNA, or 2). ligate the 3'end of target RNA to its 5' end to form a circle RNA, reverse transcribe the RNA to a cDNA, and ligate the cDNA to form a circle cDNA. The circle cDNA is amplified using a primer designed from a known sequence of a wild type target gene by rolling circle amplification or PCR methods. The known or unknown fusion gene sequences in the circle cDNA are amplified and identified by sequencing analysis.

15 Claims, 9 Drawing Sheets

Specification includes a Sequence Listing.

Amplification by rolling circle amplification method

Amplification by inverse PCR

FIG. 4

RT primer: 5'- p-CTG AGG CTC AAA GTC AGA TGC T-3' (SEQ ID NO: 1)

eb Bcr-primer: 5'- CTC CTT GTG GAT CTC GTA GAG C 3SpC3-3' (SEQ ID NO: 2)

eb ABL-primer: 5'- GGT ACC CCT TTC CAG AAG AGG G 3SpC3 -3' (SEQ ID NO: 3)

Circle cleaving primer: 5'- GACCAAAGAAGGCCAAGCTTGCCTGCCCTG-3' (SEQ ID NO: 4)

Bcr rolling primer: 5'- CAACGACCAAGAACTCTCTGGA-3' (SEQ ID NO: 5)

ABL rolling primer: AAG CCC TTC AGC GGC CAG T-3' (SEQ ID NO: 6)

Bcr F: 5'- CAA CTC CGT AGT TGT CCA CGA -3' (SEQ ID NO: 7)

Bcr R: 5'- GGA AAT GGC TGA GAA GTG CTG T -3' (SEQ ID NO: 8)

ABL F: 5'- ACT GGC CGC TGA AGG GCT-3' (SEQ ID NO: 9)

ABL R: 5'- AGCATCTGACTTTGAGCCTCA -3' (SEQ ID NO: 10)

Lane 1. Molecular size standard
Lane 2. Wild type control amplification by ABL1 inverse PCR primer set.
Lane 3. CML sample amplified by ABL1 inverse PCR primer set.
Lane 4. CML sample amplified by Bcr inverse PCR primer set
Lane 5. CML sample, no ligation, amplification by ABL1 inverse PCR primer set Lane 1. Molecular size standard
Lane 2. Circle cDNA digested with Hind III enzyme, and then amplified by ABL primer set.
Lane 3. Circle cDNA without digestion and amplified by ABL primer set.

```
                         SEQUENCE LISTING


<160> NUMBER OF SEQ ID NOS: 11

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

ctgaggctca aagtcagatg ct                                              22


<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

ctccttgtgg atctcgtaga gc                                              22


<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

ggtacccctt tccagaagag gg                                              22


<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gaccaaagaa ggccaagctt gcctgccctg                                      30


<210> SEQ ID NO 5
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 5

caacgaccaa gaactctctg ga                                              22


<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

aagcccttca gcggccagt                                                  19


<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

caactccgta gttgtccacg a                                               21


<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

ggaaatggct gagaagtgct gt                                              22


<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

actggccgct gaagggct                                                   18


<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

agcatctgac tttgagcctc a                                               21


<210> SEQ ID NO 11
<211> LENGTH: 14
<212> TYPE: RNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 11

aaaaaaaaaa aaaa                                                        14
```

METHOD FOR IDENTIFYING GENE FUSIONS BY CIRCLE CDNA AMPLIFICATION

CROSS-REFERENCE TO RELATED APPLICATIONS

This application claims benefit of and priority to U.S. Provisional Patent Application No. 62/974,193 filed on Nov. 19, 2019, which is incorporated herein by reference in its entirety.

REFERENCE TO SEQUENCE LISTING

The instant application contains a Sequence Listing which has been submitted electronically in ASCII format and is hereby incorporated by references in its entirety. Said ASCII copy, created on Dec. 21, 2020, is named 066767_001_SL.txt and is 2,790 bytes in size.

TECHNICAL FIELD OF THE INVENTION

Aspects of the invention are related to the field of nucleic acid assays, and particularly to amplification and detection of a specific target nucleic acid present in a biological sample.

BACKGROUND OF THE INVENTION

Gene fusion or translocation is one of the chromosome abnormalities that causes various genetic disorders. Unlike other types of mutations, gene fusion does not show a "hot spot" characteristic and, each case has a different fusion gene partner or the same fusion partner with a different break point at a different exon. The common methods for detecting the fusion gene include fluorescence in situ hybridization (FISH) and polymerase chain reaction (PCR). These methods require primers or probes designed from a known fusion gene. However, in many cases, a gene could have a variety of fusion partners, for example the MLL gene in leukemia is known to have over 150 identified fusion partners and potentially many unknown fusion partners. In addition, each fusion partner has a different break points. It will be difficult to design the probe or primer for identify all of these partners. A long-distance inverse PCR (LDI-PCR) method is alternative method that allow to identify the unknown fusion using a primer from known gene. This method is limited to double strand DNA, and it depend on restriction enzyme cutting site in the target gene and fusion gene. The method generate a large amount of non-fusion circle for the analysis, long distance PCR will cause the failure of amplification and sequencing. These limitations restrict the method for clinical application.

Recently next generation sequencing (NGS) has been used for the analysis of a gene fusion; however, the NGS method involves many steps, it increases the complexity of analysis, and also can generate artificial results. The NGS method is time consuming, expensive, and less efficient for the fusion analysis.

Identification of fusion partners will be useful marker for disease diagnosis, treatment monitoring, and drug development. However, there is no method that can analyze these fusion partners with a simple test in a short period of time.

Therefore, it is an object of the invention to provide an efficient method that can analyze any known or unknown fusion partner in a simple test.

SUMMARY OF THE INVENTION

One embodiment provides methods to identify known and unknown gene fusions by creating a cDNA circle and analyzing the circle cDNA by amplification or sequencing. The circle cDNA is created in two approaches: 1) reverse transcribe a target RNA to cDNA, ligate the 3'end of the cDNA to its 5'end to form a circle cDNA, or 2). ligate the 3'end of target RNA to its 5' end to form a circle RNA, reverse transcribe the circular RNA to a cDNA, and ligate the cDNA to form a circle cDNA. The circle cDNA is amplified using a primer designed from a known sequence of a wild type target gene. The known or unknown fusion gene sequences in the circle cDNA are amplified and identified by sequencing analysis.

Another embodiment provides a method to enrich the circle cDNA containing a gene. The method includes designing a primer complementary to the wild type sequences of the circular cDNA. The primer contains endonuclease recognition sequences, and the primer forms an endonuclease cleavage site within the wild type circle cDNA. The endonuclease cleaves the wild type circle cDNA but not the fusion containing circle DNA. Amplification and sequencing analysis of the un-cleaved circle cDNA will indicate the presence of a known or unknown gene fusion.

BRIEF DESCRIPTION OF THE DRAWINGS

FIG. 1A shows circular cDNA with no gene fusion. FIG. 1B shows circular cDNA with a 3' end gene fusion. FIG. 1C shows circular cDNA with a 5' end gene fusion. FIG. 1C discloses SEQ ID NO: 11.

FIG. 2A shows cleavage of circle cDNA with no fusion gene. FIG. 2B shows no cleavage of circle cDNA with a 3' end fusion. FIG. 2C shows cleavage of circle cDNA with no fusion gene. FIG. 2D shows no cleavage of circle cDNA with a 5' end fusion.

FIG. 3A shows amplification of the 3'end fusion by rolling circle amplification. FIG. 3B shows amplification of the 5' end fusion by rolling circle amplification. FIG. 3C shows amplification of 3' end fusion by inverse PCR. FIG. 3D shows amplification of 5' end fusion by inverse PCR.

FIG. 4 is a list of nucleic acid sequences used in the Examples.

DETAILED DESCRIPTION OF THE INVENTION

I. Definitions

Figure 1A:
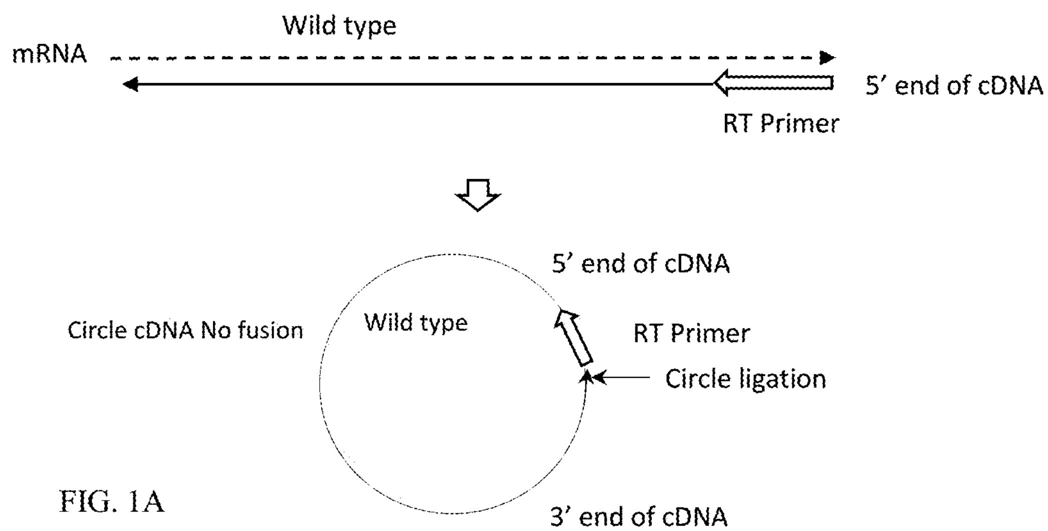
FIGS. 1A-1C are diagrams showing reverse transcription of fusion mRNA and formation of circular cDNA.
Figure 1B:
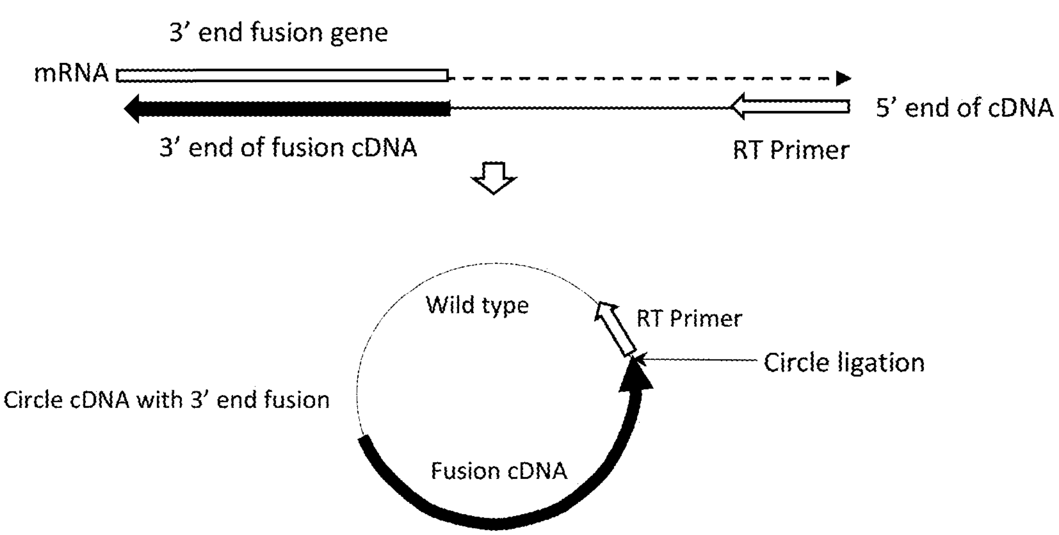
Figure 1C:
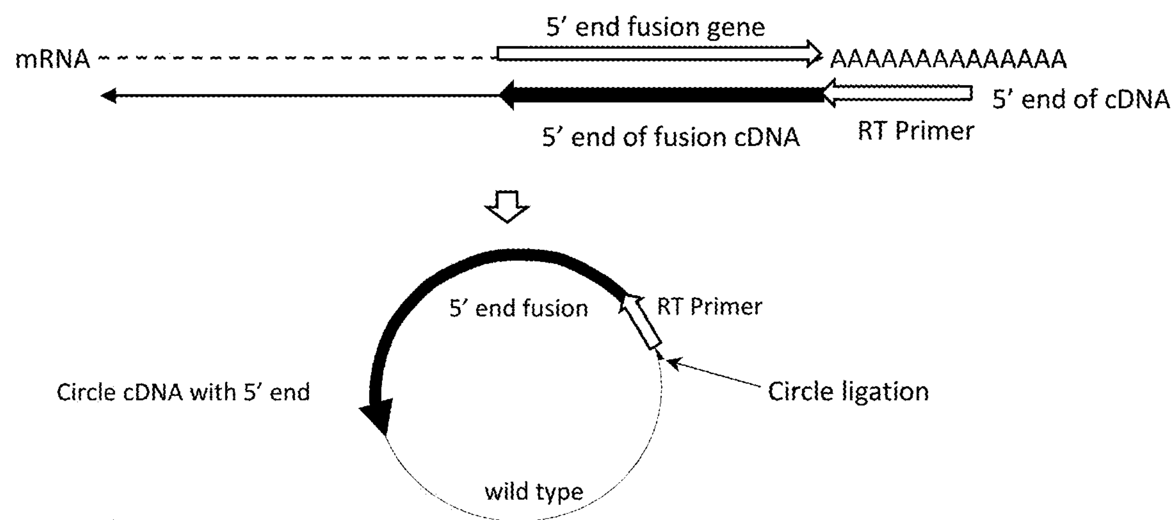
Figure 1D:
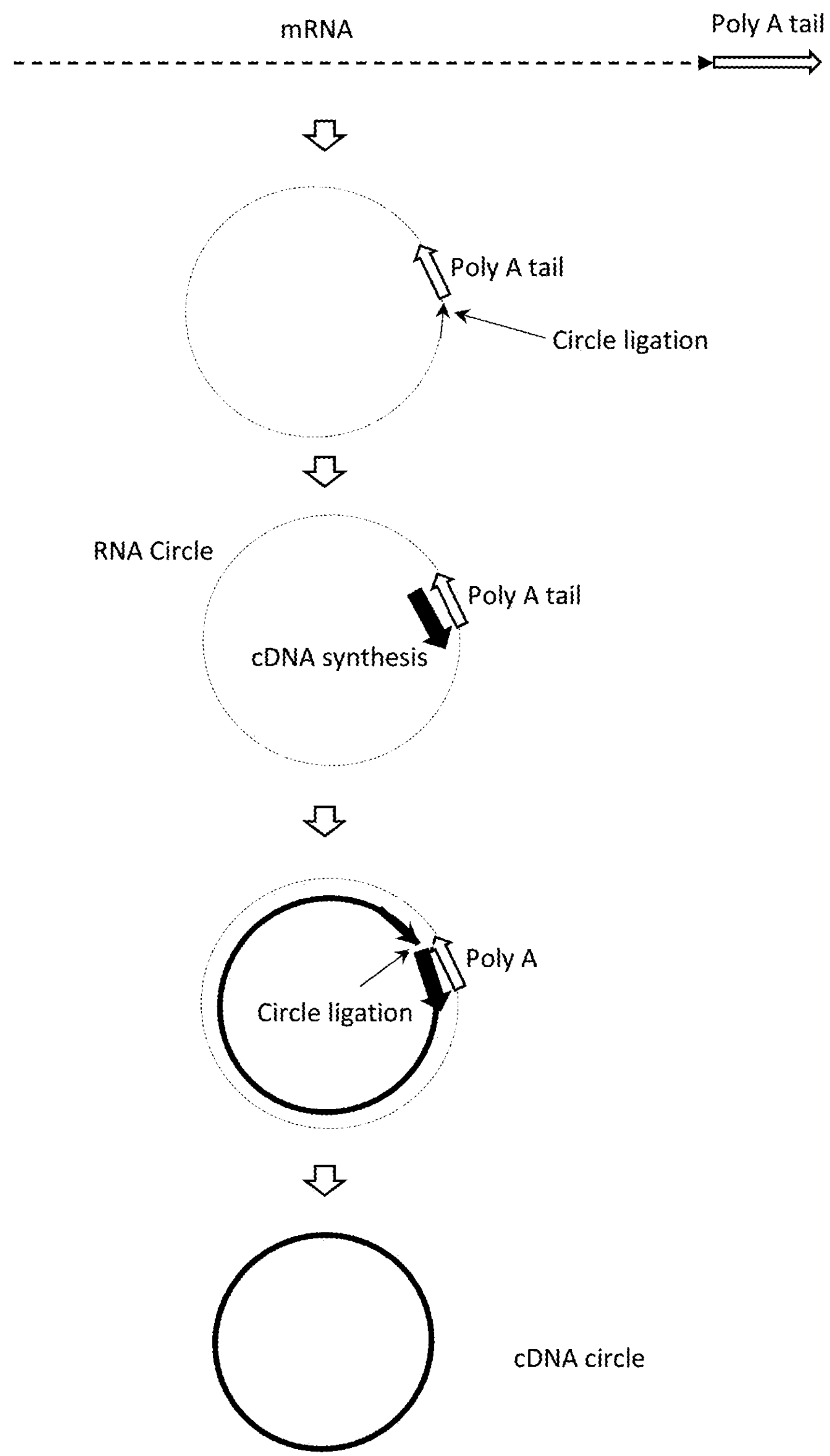
FIG. 1D shows circle cDNA formation from RNA circle.
Figure 2A:
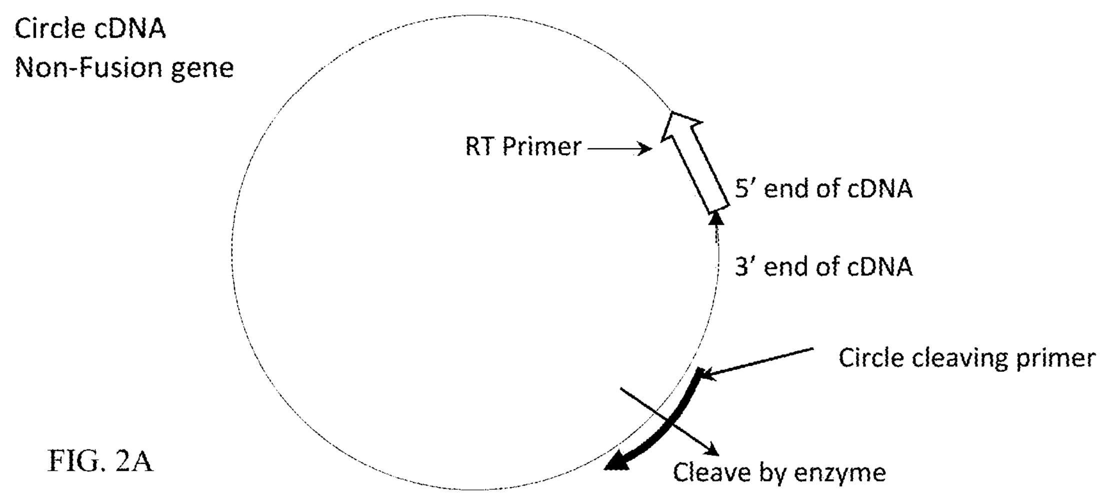
FIGS. 2A-2D are diagrams showing cleavage of Circular cDNA by using circle cleaving primer.
Figure 2B:
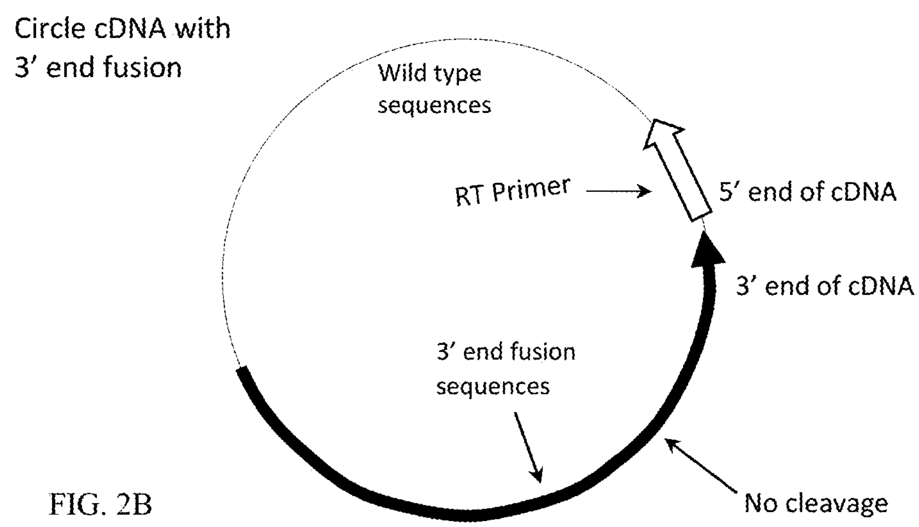
Figure 2C:
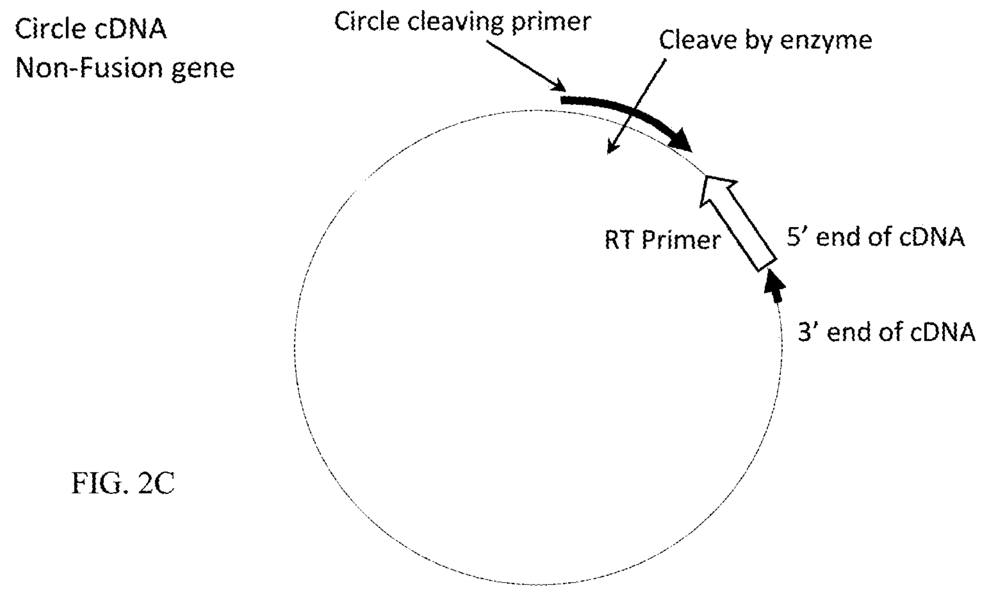
Figure 2D:
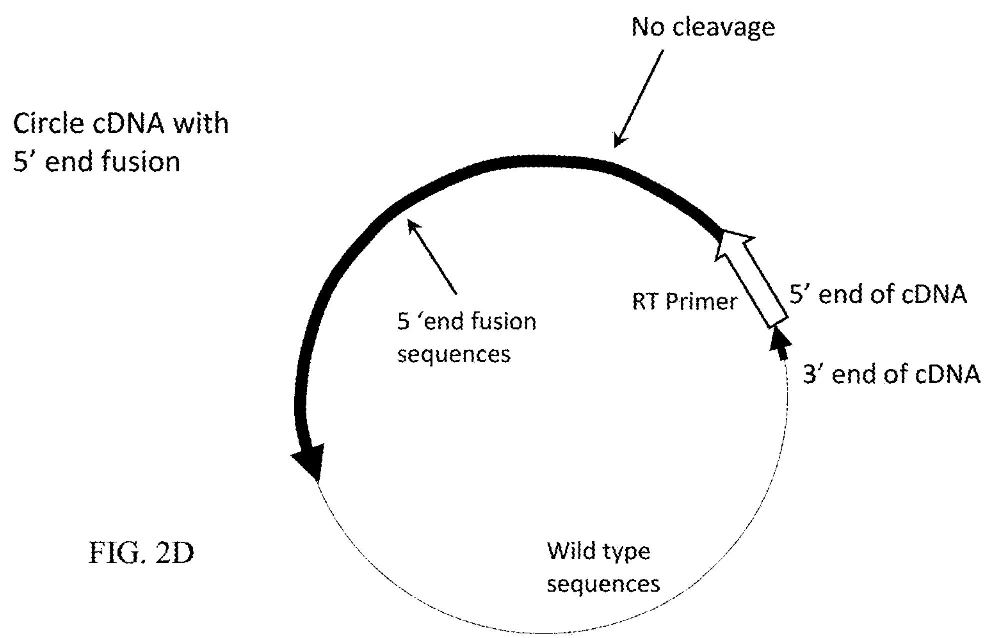
Figure 3A:
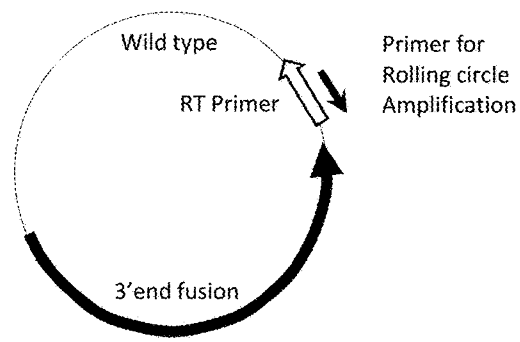
FIGS. 3A-3D are diagrams showing amplification of circular cDNA.
Figure 3B:
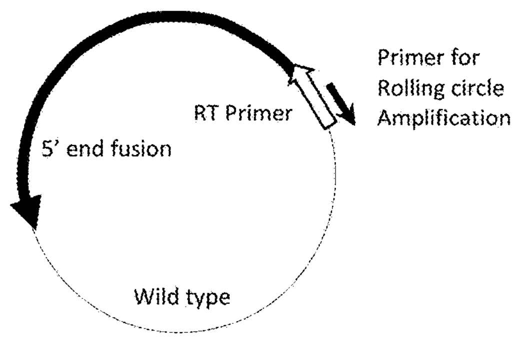
Figure 3C:
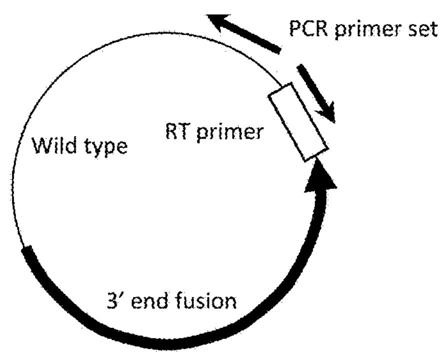
Figure 3D:
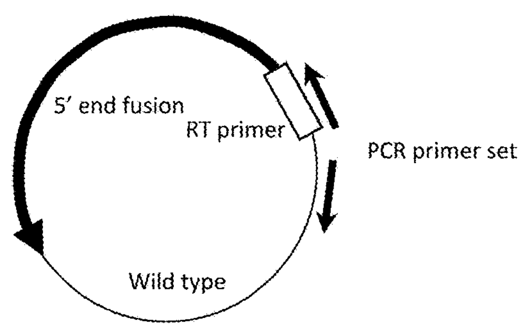

The term "nucleic acid" refers to RNA, DNA or and RNA-DNA chimera.

The term "RT" refer to reverse transcription.

The term "RT enzyme" refers to an enzyme that can using RNA as template to synthesis the cDNA including, but not limited to, M-MuLV Reverse Transcriptase and AMV reverse transcriptase.

The term "primer" refers to a fragment of DNA or DNA-RNA chimera that contains sequences complementary to target gene and used for reverse transcription or amplification.

The term "RT primer" refers to a primer used for reverse transcription.

The term "wild type gene or sequence" refers to the gene or sequence that does not contain a mutation or gene fusion sequences.

The term "5' end fusion" refers to the gene fusion partner located at the 5'end of the target gene.

The term "3' end fusion" refers to the gene fusion partner located in 3'end of the target gene.

The term "moiety" refers to a molecule that is used for labelling or modifying the RNA, DNA, or dNTPs, and includes, but not limited to, biotin, digoxigenin, a protein tag, enzyme, and a fragment of nucleic acid.

II. Detecting Gene Fusions

One embodiment discloses a method to detect known and unknown gene fusion partners in a targeted gene. The targeted gene can be RNA or DNA, preferably the targeted gene is mRNA. A RT primer is designed for reverse transcription of the targeted mRNA to synthesize cDNA. The primer has sequences that are complementary to the 3' end of the targeted mRNA or poly A tail of mRNA. In some embodiments the primer is a DNA or RNA or a DNA-RNA chimera. In one embodiment the primer has at least 6 or more nucleotides. In some embodiments, the primer is one or a group of primers. When multiple primers are used, the primers are complementary to different regions or different exons of the targeted gene. In some embodiments, the primer is modified with a moiety or moieties that that can be used for identification, isolation, ligation, amplification, and sequencing. Such a moiety may be selected from the group consisting of, but not limited to, biotin, digoxigenin, a protein tag, enzyme, and a fragment of nucleic acid. In some embodiments, the primers contain at least two portions, the sequence specific portion and adapter portion. The sequence specific portion is complementary to the targeted gene and the adapter portion contains sequence or sequences that are used for identification, isolation, amplification, and sequencing. In some embodiments the method includes hybridizing the RT primer or primers to a targeted gene to form a DNA-RNA duplex, wherein the position of hybridization is located in exons at the 3' end of targeted mRNA or poly A tail. In some embodiments, the method includes enzymatically extending the RT primer to synthesize cDNA strand. The enzyme used for this reaction is reverse transcriptase or other enzymes that can extend the DNA primer using an RNA template, include but not limited to M-MuLV Reverse Transcriptase and AMV reverse transcriptase. After the cDNA is synthesized, the method includes a step of removing the target mRNA template by using enzymatic or chemical methods such as treatment with RNase H or alkali reagents. The cDNA is then used to form a circular cDNA by using a ligase to ligate the 3'end of the cDNA to its 5'end. In some embodiments the circular cDNA is formed by an alternative method that directly ligates the 3' end of mRNA to its 5' end to form a circle RNA. The method includes hybridizing the RT primer to the circular RNA, then synthesizing cDNA by reverse transcription. The cDNA is ligated to form a circular cDNA using RNA dependent ligase.

The ligase used for circle cDNA formation is any enzyme that can ligate the 3' end of nucleic acid to the 5' end with or without a template. Exemplary enzymes include, but are not limited to CircLigase, CircLigase II, T4 DNA ligase, T4 RNA ligase, Thermostable 5' App DNA/RNA Ligase, and RtcB Ligase.

A circle cleaving primer is designed to enrich circle cDNA with fusion sequences. The primer is complementary to the non-fusion region of cDNA at the 3' downstream of RT primer. In some embodiments the primer contains endonuclease recognition sequences. To enrich the circle cDNA having a 5'end fusion, the circle cleaving primer is designed to hybridize to 5' end of non-fusion sequences of the targeted cDNA. To enrich circle cDNA having a 3' end fusion, the circle cleaving primer is designed to hybridize to the 3' end of non-fusion sequences of the targeted cDNA. The circle cleaving primer hybridizes to the circle cDNA to form a double stranded endonuclease cleavage site with the wild type circle cDNA, and then the wild type circle cDNA is cleaved by the endonuclease. Exemplary enzymes for use in this step include, but are not limited to, a restriction endonuclease, a nicking enzyme or enzyme with nick activities, zinc finger nucleases, and a CRISPR-Cas9 enzyme.

When the binding sequences of the circle cleaving primer in the circular cDNA is replaced by a fusion gene, the circle cleaving primer will no longer hybridize to the circle cDNA, and the circle cDNA will not be cleaved by the endonuclease. The enzyme used for cleaving is an endonuclease that recognizes and cleaves the duplex. In some embodiments the enzyme is any endonuclease including but not limited to specific restriction endonucleases and nicking enzymes.

The circle cleaving primer also can be a mismatch primer that contain one or more nucleotides that mismatch with wild type sequences of targeted sequences. In some embodiments the primer forms a mismatch duplex with the wild type circle cDNA, and the duplex is then recognized and cleaved by an enzyme that cleaves the mismatch sequences. Exemplary enzymes for use in this step include, but not limited to Surveyor nuclease, CEL nuclease, T4 endonuclease VII, T7 endonuclease I, and Endonuclease V.

In some embodiments the fusion enrichment step can also be performed on RNA or RNA circle by hybridizing the circle cleaving primer to targeted RNA or circle RNA at non-fusion region. In some embodiments the non-fusion circle RNA sequences are then cleaved by digestion with a DNA dependent RNase including, but not limited to RNase H.

In some embodiments the circle cleaving primer is one or more primers and has at least part of sequence complementary to the targeted cDNA or RNA. In some embodiments, the circle cleaving primer is modified with a moiety to block primer extension or aids in isolation and/or detection. In some embodiments the circular cDNA is then amplified by rolling circle amplification or PCR methods. In some embodiments the primer for amplification is designed to hybridize to a non-fusion portion of the targeted cDNA or RT primer. To detect cDNA with a 5' end fusion gene, the amplification primer is located in the 3' end non-fusion region of the cDNA. To detect cDNA with a 3' end fusion gene, the amplification primer is located in the 5' end non-fusion region of the cDNA.

For the rolling circle amplification method, a primer is designed to be complementary to RT primers or any non-fusion region of the targeted circle cDNA. The rolling circle amplification method may be performed by a polymerase that has strand displacement activity such as Phi29 polymerase, Bst large fragment, and T7 RNA polymerase. For the PCR method, a set of inverse primers is designed in the non-fusion region, the forward primer is complementary to the sequence of non-fusion cDNA and reverse primer is flanking to forward primer and has sequence identical to the non-fusion cDNA, the polymerase extend the forward primer using the circle cDNA as template, the extension will crossover the ligation point and ended at 5' end of the forward primer, the reverse primer will hybridize to the 3' end of the extended strand and duplicate the strand.

In some embodiments the amplified products are analyzed by any sequencing method, and the sequence results indicate the presence of known or unknown gene fusion partners. To perform sequencing analysis, the RT primer or amplification primer are designed to have a portion that contains an adapter sequence for sequencing. The rolling circle amplification product can be directly applied to the third generation sequencing analysis such as Nanopore® sequencing technique through the adapter sequence on the RT primer or rolling circle amplification primers. The PCR product can be analyzed by next generation sequencing through the adapter sequence of RT primer or rolling circle amplification primers.

Another embodiment provides a kit containing all the reagents needed to detect a gene fusion using the methods disclose herein, for example the reagents used in the Examples and described herein. In one embodiment, the kit includes primers, reverse transcriptase enzymes, detection labels such as fluorescent labels, endonucleases, and buffers in a container. In one embodiment, the kit includes written instructions for detecting a gene fusion using the methods disclosed herein.

EXAMPLES

Example 1: Identification of Fusion by cDNA Circle Ligation and Amplification Materials and Methods A cell line sample from a CML patient characterized by the translocation t(9;22)(q34;q11.2) was used for this experiment, the cell line was previously determined as a Bcr (exon 6) -ABL1 (Exon 2) fusion. The RNA was extracted using a commercial RNA extraction kit (Qiagen®) and final elution volume was 50 μl. 10 μl of the final eluate was used for reverse transcription (RT). The RT primer was designed to be complementary to exon 2 of the ABL1 gene (FIG. 4). Two extension blocking primers (eb primer) were designed to block the further extension of the RT primer on the Bcr and ABL1 gene. The eb-Bcr primer is complementary to exon 4 of Bcr gene, and the eb-ABL1 primer is complementary to exon 1 of ABL1 gene (FIG. 4). The final concentration of the primers in the RT mix was 300 nM for RT primer and 600 nM for eb-primers. The RT reaction was performed at 37° C. for 1 hour using a commercial First strand cDNA synthesis kit (New England Biolab).

After reverse transcription, 1 μl of RNase H (New England Biolab) was added to the reaction mix and incubated at 37° C. for 30 minutes. The enzymes were then inactivated by heating the reaction mix at 95° C. for 5 minutes. The circle cDNA formation was performed by using Circligase™, and the total reaction volume was 20 μl including 15 μl of the RT reaction mix, 1× ligation buffer, 2.5 mM MnCl, 10U Circligase II (Lucigen™). The mixture was then incubate at 60° C. for 2 hours.

After ligation, the circle cDNA was amplified by rolling cycle amplification and PCR methods. For rolling circle amplification, a single primer (rolling primer) was designed for either the ABL1 gene or for the Bcr gene. The ABL1 rolling primer is complementary to exon 2 of ABL1 cDNA, and the Bcr rolling primer is complementary to exon 6 of Bcr cDNA. The amplification was performed in 50 μl of reaction mix including rolling primers, QuantiFluor® dye, dNTP, reaction buffer, phi29 DNA polymerase and 10 μl of final ligation products. The reaction was performed at 30° C. for 45 minutes in a real-time thermocycler.

The circle cDNA was also amplified by a PCR method. An inverse primer set was designed to specifically amplify the circle cDNA. The position of the ABL1 primer set was located at exon 2 of the ABL1cDNA, and the forward primer was complementary to the sequence of the RT primer. The reverse primer has sequence identical to the cDNA downstream of the flanking sequence of the RT primer.

Results

Figure 5A:
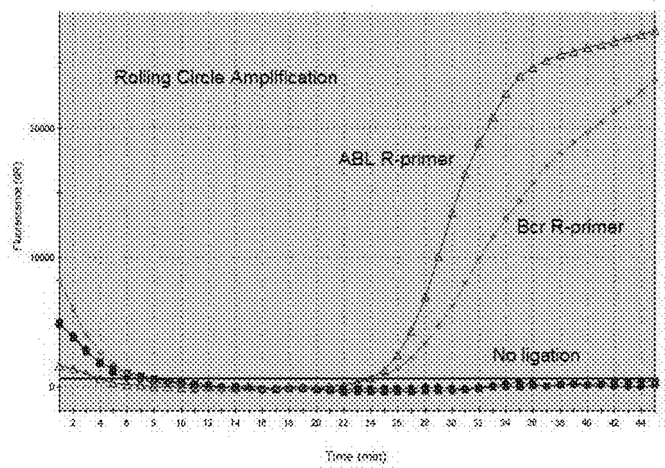
FIG. 5A is a line graph of Fluorescence versus Time (min.) showing results of rolling circle amplification using the ABL1R-primer (▲), the Bcr R-primer (*) and a control.

Both rolling primers show amplification. The amplification products are represented by the fluorescent intensity of single strand DNA/RNA binding dye. The amplification by ABL1 rolling-primer representing the amplification of the circle cDNA contains the ABL1 gene only and the circle contains ABL-Bcr fusion gene. The signal amplified by the Bcr rolling primer representing the amplification of Bcr-ABL1 gene fusion (FIG. 5A). The un-ligated cDNA was used as an amplification control and there was no amplification from both primers (FIG. 5A). The results indicated that the method able to amplify the fusion gene by using a single primer from the known sequence of target gene.

Figure 5B:
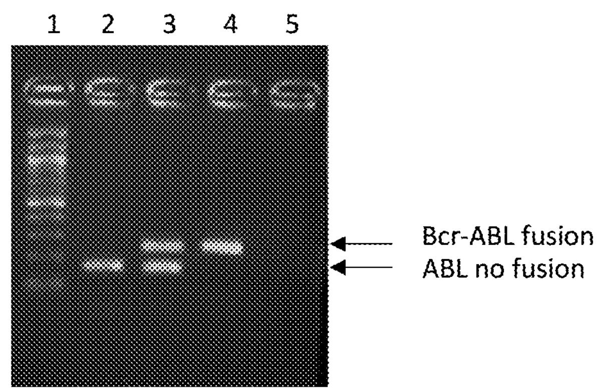
FIG. 5B is a photograph of a gel showing amplification by inverse PCR.
Figure 6:
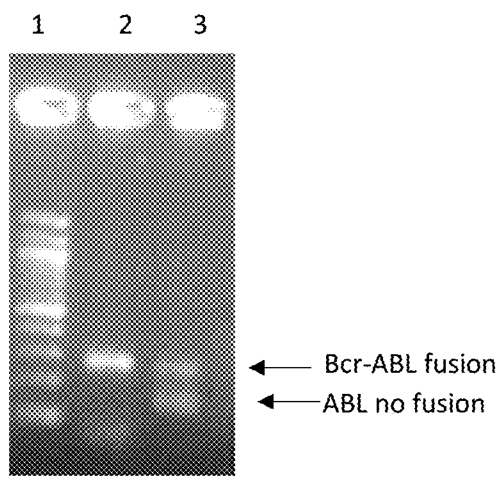
FIG. 6 is a photograph of a gel showing enrichment of the cDNA containing a fusion.

The PCR amplification of circle cDNA shows two different amplification products. The 190 bp product is amplification of wild type of ABL1 gene include partial sequences of exon 2 and exon 1. This amplification is confirmed by wild type samples and the Bcr-ABL1 fusion samples. The 285 bp product is amplification of Bcr-ABL1 fusion gene include partial sequences of exon 2 of ABL1 gene and exon 6 exon 5 and exon 4 of the Bcr gene. (FIG. 5B). The amplification of Bcr fusion gene by ABL1 PCR is also confirmed by using Bcr specific inverse PCR primers designed to exon 5 of Bcr gene. These is no amplification is observed in the unligated samples. The amplification of ABL1 inverse primers set indicated the cDNA circle contains Bcr-ABL1 fusion gene.

Example 2: Enrichment of Fusion cDNA Circle

Materials and Method

The circle cDNA was generated using the procedures disclosed in Example 1. The circle ligation generated two different types of circle cDNA from fusion sample. One type contains only the wild type sequence (wild type circle), and another contains the fusion gene. To enrich the circle cDNA having the fusion gene, a circle cleaving primer was designed to cleave the wild type circle. The primer is complementary to exon 1 of ABL1 gene. After circle formation, 1 μl of the circle cleaving primer was added (final concentration 300 nM) to 15 μl of circle cDNA and mixed. The mixture was heated at 95° C. for 3 minutes. The primer was annealed at 50° C. for 10 minutes to form a duplex with the wild type circle and create a Hind III recognition site. The duplex was then digested in a reaction mix including Hind III and exonuclease (New England Bio Labs) at 37° C.

for 1 hour to cleave the wild type circle. To stop the enzyme digestion, the sample was heated at 95° C. for 5 minutes to inactive the enzymes. The circle cDNA mix was then subjected to inverse PCR amplification. The PCR primer set used for amplification were the same primer sets used in Example 1.

Results

The results show that the amplification of wild type ABL1 gene disappeared after enzyme digestion. However, the amplification of the Bcr-ABL1 fusion gene was not affected or enhanced. The results indicate that the wild type circle cDNA is removed from the cDNA mix by the enzyme treatment. The circle cDNA contains Bcr-ABL1 fusion gene is enriched in the cDNA mix and more efficiently amplified.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

What is claimed:

1. A method to detect known and unknown gene fusions comprising:

a) providing a reverse transcription (RT) primer complementary to a sequence at a 3' end or poly A tail of a targeted ribonucleic acid (RNA);

b) hybridizing the RT primer to the targeted RNA to form a DNA-RNA duplex, wherein the RT primer is complementary to a sequence at a 3' end or poly A tail of the targeted RNA;

c) enzymatically synthesizing cDNA by RT;

d) ligating the 3'end of the cDNA to its 5'end to form a circular cDNA;

e) providing a circle-cleaving primer having a sequence complementary to non-fusion sequences of a targeted cDNA downstream of the RT primer, wherein the circle-cleaving primer contains sequences that can be recognized and cleaved by an endonuclease;

f) hybridizing the circle-cleaving primer to a region suspected of having a gene fusion in the circular cDNA to form an endonuclease cleavage site;

g) cleaving non-fusion circular cDNA with an endonuclease;

h) amplifying uncleaved circular cDNA using rolling circle amplification or PCR methods; and, i) detecting a gene fusion by amplification or sequencing analysis of the amplified products.

2. The method of claim 1, wherein the RT primer comprises DNA or a DNA-RNA chimera and has at least 6 nucleotides.

3. The method of claim 1, wherein the RT primer is one primer or a group of primers, and wherein RT primers in the group of primers are complementary to different regions or different exons of the targeted RNA.

4. The method of claim 1, wherein the RT primer is modified with a moiety for the purpose of isolation, ligation, amplification, sequencing or detection.

5. The method of claim 4, wherein the moiety is selected from the group consisting of biotin, digoxigenin, a protein tag, an enzyme, and a fragment of nucleic acid.

6. The method of claim 1, wherein the endonuclease is selected from the group consisting of a restriction endonuclease, a nicking enzyme or enzyme with nick activities, zinc finger nucleases, and a CRISPR-Cas9 enzyme.

7. The method of claim 1, wherein the circle-cleaving primer comprises a sequence that mismatches with fusion-containing cDNA, and forms mismatched DNA-DNA duplexes with the circular cDNA.

8. The method of claim 7, wherein the mismatched DNA-DNA duplexes are cleaved by an enzyme that recognizes and cleaves all types of mismatch sequences selected from the group consisting of T4 endonuclease VII, T7 endonuclease I, and CEL nuclease.

9. The method of claim 1, wherein the ligation is performed by an enzyme that can ligate a 3' end of single-stranded nucleic acid to its 5' end to form a circular nucleic acid selected from a group consisting of T4 DNA ligase, T4 RNA ligase, Thermostable 5' App DNA/RNA Ligase, and RtcB Ligase.

10. The method of claim 1, wherein the amplification of the un-cleaved circular DNA is performed by rolling circle amplification with a primer complementary to non-fusion sequences of the circular DNA.

11. The method of claim 10, wherein the amplification of the un-cleaved circular DNA is performed by a polymerase that has strand displacement activity selected from a group consisting of Phi29 polymerase, Bst large fragment, and T7 RNA polymerase.

12. The method of claim 1, wherein the amplification of the un-cleaved circular DNA is performed by PCR using primers complementary to the targeted cDNA.

13. The method of claim 1, wherein an RT primer or an amplification primer used in the sequencing analysis comprises an adapter sequence.

14. A method to detect known and unknown gene fusions comprising:

a) ligating the 3'end of an mRNA to its 5'end to form a circular mRNA;

b) hybridizing an RT primer to the circular mRNA to form a DNA-RNA duplex;

c) extending the RT primer by reverse transcription to synthesize cDNA;

d) ligating the 3'end of the cDNA to its 5'end to form a circular cDNA;

e) hybridizing a circle-cleaving primer to a region suspected of having a gene fusion in the circular cDNA to form an endonuclease cleavage site, wherein the circle-cleaving primer has sequences complementary to non-fusion sequences of a targeted cDNA downstream of the RT primer and the circle-cleaving primer contains sequences recognized by an endonuclease;

f) enzymatically cleaving non-fusion circular cDNA with the endonuclease;

g) amplifying uncleaved circular cDNA using rolling circle amplification or PCR methods; and h) detecting a gene fusion by amplification or sequence analysis of the amplified products.

15. The method of claim 14, wherein the circle-cleaving primer hybridizes to an RNA circle to form a DNA-RNA duplex and the RNA circle is cleaved by digestion by a DNA-dependent RNase.

* * * * *